United States Patent [19]

Innes

[11] 4,118,433

[45] Oct. 3, 1978

[54] ISOPARAFFIN-OLEFIN HF ALKYLATION PROMOTED WITH TRIFLUOROMETHANESULFONIC ACID

[75] Inventor: Robert A. Innes, Wilkins Township, Allegheny County, Pa.

[73] Assignee: Gulf Research & Development Company, Pittsburgh, Pa.

[21] Appl. No.: 501,664

[22] Filed: Aug. 29, 1974

Related U.S. Application Data

[63] Continuation-in-part of Ser. No. 362,425, May 21, 1973, abandoned.

[51] Int. Cl.² ............................................. C07C 3/54
[52] U.S. Cl. ............................................. 260/683.51
[58] Field of Search .................... 260/683.47, 683.51, 260/683.58, 683.48

[56] References Cited

U.S. PATENT DOCUMENTS

| 2,313,103 | 3/1943 | Thomas | 260/683.47 |
|---|---|---|---|
| 2,317,694 | 4/1943 | Ott | 260/683.47 |
| 2,325,052 | 7/1943 | Grosse et al. | 260/683.48 |
| 2,570,574 | 10/1951 | Linn | 260/683.48 |
| 3,778,489 | 12/1973 | Parker et al. | 260/683.47 |

*Primary Examiner*—George Crasanakis

[57] ABSTRACT

The hydrogen fluoride catalyzed alkylation of isoparaffins such as isobutane with monoolefins such as propylene is promoted utilizing small amounts of trifluoromethanesulfonic acid or fluorosulfonic acid.

8 Claims, 1 Drawing Figure

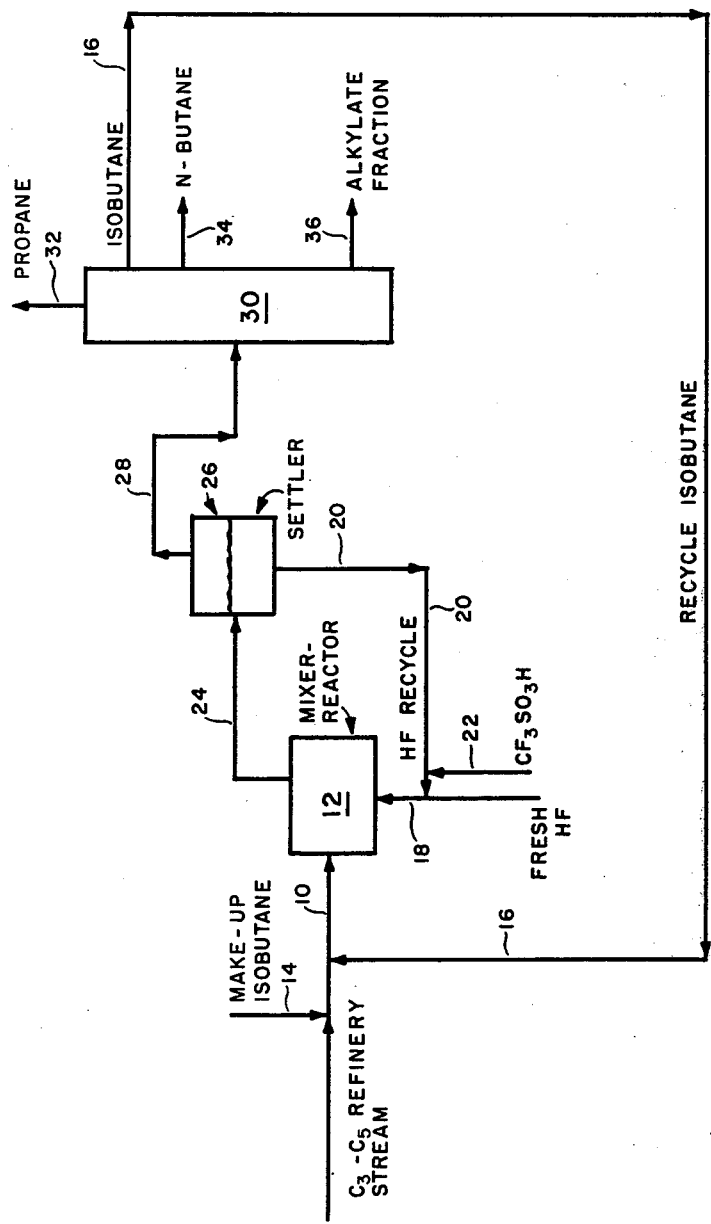

ISOPARAFFIN-OLEFIN HF ALKYLATION PROMOTED WITH TRIFLUOROMETHANESULFONIC ACID

This invention relates to the alkylation of isoparaffins with olefins and more particularly to the improvement in the hydrogen fluoride catalyzed alkylation of isoparaffins using a promoting amount of trifluoromethanesulfonic acid or fluorosulfonic acid.

This application is a continuation-in-part of our co-pending Ser. No. 362,425, filed May 21, 1973, and now abandoned and assigned to the same assignee as the present application.

The alkylation of isoparaffinic hydrocarbons with olefins in the presence of strong acid catalysts such as liquid HF is well known in the art. In the prior art, U.S. Pat. No. 3,778,489 to Parket et al. suggests the use of various strong acid catalysts for the alkylation of paraffins with olefins. The strong acid catalysts suggested by Parker et al include sulfuric acid; hydrogen fluoride; halosulfuric acid, such as fluorosulfuric acid; trihalomethanesulfonic acid, such as trifluoromethanesulfonic acid. Parker et al further suggest that the strong acid catalyzed reaction can be promoted with varying quantities of water, alcohols, thiols, ethers and other materials. Despite Parker et al.'s suggestion that $CF_3SO_3H$ can be used as a catalyst for the reaction, Parker et al provide no working examples using $CF_3SO_3H$. In fact, the only two working examples in Parker et al employ $FSO_3H$ as the catalyst promoted with 20 mole percent water. There are no runs showing the effect of $FSO_3H$ alone.

As will be shown later, $FSO_3H$ and $CF_3SO_3H$ are each, alone, rather poor alkylation catalysts.

From a commercial standpoint, HF has certainly been the catalyst of choice for the alkylation of paraffins with olefins. Considerable research effort has been and continues to be expanded over the years to discover means to improve the HF alkylation reaction to achieve a faster reaction at lower temperatures, increased alkylate yield and increased alkylate quality as measured by octane number.

In accordance with the invention, an improved alkylation process has been achieved wherein an isoparaffin having from 4 to 5 carbon atoms per molecule is alkylated with an olefinic hydrocarbon charge stock comprising at least 1 monoolefin selected from the group consisting of propylene, butene-1, pentene-1 and hexene-1. The process comprises reacting at least one of said isoparaffins with at least one of said monoolefins in the presence of a catalyst system comprising hydrogen fluoride and a promoting amount of a fluorinated sulfonic acid selected from the group consisting of fluorosulfonic acid and trifluoromethanesulfonic acid under reaction conditions including a temperature from $-20°$ C. to $30°$ c. and a reaction pressure sufficient to maintain the hydrogen fluoride in the liquid phase.

The isoparaffin component of the charge stock for this reaction suitably has from 4 to 5 carbon atoms per molecule. By an "isoparaffin" is meant a saturated aliphatic hydrocarbon having a methyl group on the next-to-terminal carbon atom, i.e. the beta carbon atoms and no other branches. Thus the isoparaffin can suitably by isobutane or isopentane or mixtures of the two. Isobutane is the preferred isoparaffin. Other paraffinic hydrocarbons boiling in about the same range can also be present in the charge stock. Normal paraffins such as propane, n-butane and n-pentane are essentially inert.

The isoparaffin is alkylated with an olefinic hydrocarbon charge stock comprising a monoolefin selected from the group consisting of propylene, butene-1, pentene-1 and hexene-1 or mixtures of these straight-chain alpha-olefins. Usually the olefinic hydrocarbon charge stock contains from 10 to 100 weight percent, preferably from 25 to 100 weight percent, of the straight-chain alpha-olefin having from 3 to 6 carbon atoms per molecule. Internal or branched-chain monoolefins may also be present, e.g. isobutylene and butene-2.

The most preferred charge stocks for the process of this invention are the so-called $C_3$, $C_4$ and $C_5$ refinery streams or combinations of these streams, e.g. $C_3$–$C_4$ or $C_3$–$C_5$, derived from the catalytic cracking of petroleum hydrocarbons. A typical composition of a $C_3$–$C_5$ refinery stream is shown on Table IV below.

As is well known, the olefinic component enters the reaction zone in a much lower concentration than the isoparaffinic component since olefins are subject to many undesirable side reactions such as polymerization. The molar ratio of the isoparaffins to olefins entering the reaction zone can be from 5:1 to 100:1 but is usually from 8:1 to about 20:1. This high ratio of isoparaffin to olefin in the charge stock is usually maintained by a suitable recycle operation.

The alkylation reaction is catalyzed using liquid HF. The volume ratio of the hydrocarbon charge (both isoparaffin and olefin) to the acid catalyst can be from 0.1:1 to 10:1, is usually from 0.5:1 to 2:1. By "acid catalyst" is meant the combined volume of HF plus fluorinated sulfonic acid promoter employed.

The alkylation reaction temperature can suitably be from $-20°$ C. to $30°$ C., although it has been found that preferred reaction temperatures for the process of this invention are in the range of $0°$ C. to $25°$ C., more preferably from $0°$ C. to $20°$ C. The reaction pressure must be sufficient to maintain the HF in the liquid phase, and such pressure is usually from 2 to 20 atmospheres.

The reaction is usually run in a continuous stirred tank or plug flow type reactor with the hydrocarbons and the catalyst continuously added and removed. The reactor is usually sized to provide a residence time in the reactor of from 0.1 to 10 minutes, preferably from 0.5 to 5.0 minutes. This translates to a liquid hourly space velocity of from 6 to 600; preferably a liquid hourly space velocity of 12 to 120; where "liquid hourly space velocity" is defined as the volume of hydrocarbon plus HF acid entering the reactor per hour, divided by the volume of the reactor.

It is well known that the hydrocarbon charge stock and the liquid hydrogen fluoride are immiscible and intimate phase contacting is necessary to insure a reasonably efficient reaction. Intimate phase contacting is achieved by vigorous mixing. The contacting of acid and hydrocarbon phases can be accomplished by methods well known in the art, such as by mixing nozzles, ultrasonic mixers, etc. The reactor is designed so that intimate mixing occurs at the inlet to the reactor in order to promote the desired alkylation reaction and avoid the undesirable side reactions such as olefin polymerization.

A typical processing scheme utilizing $CF_3SO_3H$ as the promoter is shown on the attached Figure. Referring to the Figure, a $C_3$–$C_5$ refinery stream enters through line 10 into mixer-reactor 12. The refinery $C_3$–$C_5$ charge stock contains both isoparaffin components and olefin components. A typical $C_3$–$C_5$ refinery stream is shown on Table V below. However, the molar ratio of the isoparaffins to olefins must normally be adjusted by the addition of isoparaffin to bring the molar ratio of isoparaffin to olefin within the desired range. As noted above, the molar ratio of isoparaffin to olefin entering the reaction zone is normally from 5:1 to 100:1. It is preferred to adjust the isoparaffin to olefin ratio with isobutane. In the reaction zone the olefins in the $C_3-C_5$ refinery stream tend to alkylate exclusively with the isobutane due to the large excess of isobutane and its more reactive nature compared to isopentane. The molar ratio of isobutane to olefin is normally adjusted in two ways, i.e. makeup isobutane is added through line 4 so that the isobutane to olefin molar ratio in the $C_3-C_5$ refinery stream is about 1:1 and by the further addition of recycle isobutane through line 16 to increase the isobutane to olefin ratio to within the desired range. The hydrogen fluoride enters mixer-reactor 12 through line 18. The HF is made up of fresh HF and recycle HF from line 20. The trifluoromethanesulfonic acid can suitably be added to the recycle HF stream through line 22 or can, if desired, be added with the fresh HF. The products from the mixer-reactor 12 are removed through line 24 and enter settler 26, where the acid phase settles to the bottom and is removed through line 20 for recycle to line 18. A small slipstream of the recycle acid (not shown) is sent to a regenerator (not shown) where dissolved alkyl fluorides are decomposed and the acid is separated from any accumulated water and heavy polymers. The hydrocarbon products are removed from settler 26 through line 28 and are sent to distillation column 30, such as propane through line 32; isobutane through line 16; n-butane through line 34; and an alkyalte fraction through line 36. The isobutane is normally recycled to be admixed with the $C_3-C_5$ refinery stream in line 10. The other distillate fractions may be suitably treated such as with caustic to remove traces of hydrogen fluoride.

It has been found in accordance with the invention that small amounts of a fluorinated sulfonic acid promoter selected from the class consisting of fluorosulfonic acid ($FSO_3H$) and trifluoromethanesulfonic acid ($CF_3SO_3H$) promote the alkylation of isoparaffins with olefins by increasing the rate of the alkylation reaction. In addition, the efficiency of the reaction as observed by an increase in the yield of alkylate product and/or an increase in the research octane number (RON) of the alkylate product can be obtained.

A promoting effect has been observed utilizing as little as 0.1 weight percent of a fluorinated sulfonic acid selected from the group consisting of fluorosulfonic acid and trifluoromethanesulfonic acid, but usually from 2 to 30 weight percent of the fluorinated sulfonic acid promoter is used based on the total weight of HF and promoter employed. The most preferred concentration of promoter is from 4 to 20 weight precent. Fluorosulfonic acid is also known as fluorosulfuric acid. Trifluoromethanesulfonic acid is sometimes referred to as trimsylate acid. The optimum amount of promoter will depend upon the particular reaction conditions and charge stock employed and by the desired results, e.g. improved yields or RON of the product. For example, alkylating isobutane with a refinery $C_3-C_5$ olefin feed at 4° C., the optimum amount of trifluoromethanesulfonic acid was about 6.5 weight percent of the total amount of HF—$CF_3SO_3H$ whereas the optimum amount of $FSO_3H$ under the same conditions was about 9.7 weight percent. In any case, the optimum amount can be ascertained by one having ordinary skill in this art by a few simple routine experiments. In general, to achieve an improved Research octane number, the optimum amount of promoter decreases as the temperature increases. Also, at any given temperature, the concentration of $FSO_3H$ or $CF_3SO_3H$ reaches a level within the ranges defined above where further increases in concentration result in no added beneficial effects. So far as increased yields of alkylate product are concerned, improved yields are obtained as the concentration of $FSO_3H$ or $CF_3SO_3H$ increases at those conditions of temperature and space velocity where olefin conversion is incomplete. Thus at the lower temperatures and/or higher space velocities, increased concentrations of the promoter of this invention within the ranges defined above are preferred in order to obtain increased yields of alkylate product. In all cases the presence of fluorosulfonic or trifluoromethanesulfonic acid increases the rate of reaction so long as the concentration of $FSO_3H$ or $CF_3SO_3H$ is within the ranges defined above. The effect of the fluorosulfonic or trifluoromethanesulfonic acid on the rate of reaction is most clearly seen in the preferred lower temperature ranges of 0° C. to 25° C.

The invention will be further described with reference to the following experimental work.

In most of the runs for the experiments which are described below, the following procedure was used:

Blends of isobutane with various olefinic feedstocks were prepared and stored as liquids in LPG cylinders under nitrogen pressure. The reaction was carried out in a continuous flow system. The feed blend was pumped at a calibrated rate into a stainless steel autoclave containing liquid hydrogen fluoride; $FSO_3H$; $CF_3SO_3H$; or blends of liquid HF and either $CF_3SO_3H$ or $FSO_3H$. Temperature was controlled by passing water from a controlled temperature reservoir through the jacket of the autoclave. In all runs, except where otherwise indicated, the reaction time was three hours. The autoclave was stirred at 1600 rpm, intimately mixing the acid and hydrocarbon phases, causing the alkylation reaction to be catalyzed. A stream (emulsion) of acid-hydrocarbon mix was continuously removed from the autoclave to a settler. The acid settled to the bottom of the settler and was continuously returned by gravity flow through a stainless steel line to the autoclave. The acid level in the settler was adjusted so that the autoclave contained approximately equal volumes of hydrocarbon and acid. The hydrocarbon product passed out the top of the settler through a valve which controlled the pressure in the autoclave at 200 psig. The product then passed through a bed of Ascarite to remove dissolved HF and was collected in a trap at −78° C.

All hydrocarbon analyses were made by gas chromatography. Products were identified on the basis of their retention times. Response factors were determined experimentally using synthetic blends of pure compounds. These blends closely resembled actual alkylation feeds and products. All chromatographs were connected to a Perkin Elmer PEP-1 chromatographic data processing system which determined peak areas and calculated the results.

Feedstocks were analyzed using a Varian model 1800 gas chromatograph with a thermal conductivity detector and a 10′ × ¼″ O.D. silver nitrate - benzyl cyanide on chromosorb column at 30° C.

Products were analyzed using a Varian model 1800 gas chromatograh with a flame ionization detector and a 200′ × .01″ I.D. squalane-coated capillary column at 27° C. In order to determine accurately the percentage of heavies in the alkylate, the product was also analyzed using a Varian model 200 gas chromatograph with a thermal conductivity detector and a 10' × ¼" O.D. 25% hexatriacontane on chromosorb R column at 80° C. After the C₈'s had been eluted, the column was backflushed through the detector and the temperature was increased to 120° C. to obtain the heavy products. Normal hexane was added to the product as an internal standard except in those cases where the octane number of the product was to be determined on a test engine.

In some cases the excess isobutane was then distilled off, and the research octane number of the alkylate fraction was determined on a test engine. Three or four runs were made at each set of conditions, and the data shown represent the arithmetic average for these runs. The precision of the RON data, both estimated (i.e. calculated) and experimental, is ± 0.3 at the 95% confidence level.

A first series of runs was made illustrating the alkylation of isobutane with propylene using liquid HF as the catalyst promoted with varying amounts of trifluoromethanesulfonic acid. As noted above, the volume ratio of liquid HF (or HF + CF$_3$SO$_3$H) to hydrocarbons in the reactor was about 1:1. These results are summarized in Table I below. The feedstock for the runs in Table I consisted of 95 weight percent isobutane and 5.0 weight percent propylene.

TABLE I
PROMOTION OF
ISOBUTANE/PROPYLENE ALKYLATION
WITH TRIFLUOROMETHANESULFONIC ACID

| Ex. No. | 1 | 2 | 3 | 4 | 5 | 6 |
|---|---|---|---|---|---|---|
| Wt % CF$_3$SO$_3$H | 0 | 3.8 | 3.8 | 6.6 | 6.6 | 6.6 |
| LHSV | 20 | 20 | 40 | 20 | 40 | 80 |
| Temp. ° C. | 2 | 2.5 | 3 | 4 | 5 | 4.5 |
| % Yield | 176 | 199 | 180 | 230 | 212 | 165 |
| Estimated RON | 90.8 | 92.8 | 92.2 | 93.5 | 92.8 | 92.2 |
| Alkylate Composition (wt %) | | | | | | |
| Isopentane | 1.7 | 2.5 | 2.1 | 2.5 | 3.1 | 3.3 |
| Hexanes | 1.3 | 2.2 | 2.0 | 2.4 | 2.8 | 3.1 |
| 2,4-dimethylpentane | 3.9 | 9.9 | 6.8 | 12.2 | 12.0 | 10.1 |
| 2,3-dimethylpentane | 77.0 | 51.8 | 60.7 | 41.6 | 44.4 | 52.5 |
| Trimethylpentanes | 9.5 | 30.3 | 23.1 | 37.5 | 32.6 | 25.6 |
| Dimethylhexanes | 0.8 | 1.5 | 1.2 | 1.8 | 1.8 | 2.4 |
| Heavies | 6.3 | 2.1 | 3.9 | 2.0 | 3.3 | 3.0 |

Referring to Table I, the most valuable components from an octane standpoint are the trimethylpentanes. It can be seen by a comparison of the Examples that the addition of the promoter of this invention results in an increase in trimethylpentanes from 9.5 weight percent of the product (Example 1) to as much as 37.5 weight percent of product (Example 4). In addition, the percent yield has also increased utilizing the promoter of this invention as is shown by a comparison of Examples 1 and 4. The theoretical percent yield is 238. By "theoretical percent yield" is meant the amount of alkylate which would be obtained if each molecule of olefin reacted on a 1:1 basis with isobutane. By "alkylate" is meant the product having at least one more carbon atom than the reacting isoparaffin in the charge stock. The "% Yield" figures were calculated in Table I by dividing the weight of the alkylate obtained by the weight of olefins in the feed and multiplying by 100. Achieving a yield close to the theoretical shows not only substantially complete conversion of the olefinic component but also improved reaction efficiency by conversion of the olefin to the desired one-to-one paraffinolefin alkylate. The "Estimated RON" means a calculated weighted average octane member based on the composition of the alkylate actually obtained using ASTM values of RON for the pure components. It can be seen that using the promoters of this invention, one to two octane number increases in the product can be obtained.

A second series of runs, similar to the first series, was made illustrating the alkylation of isobutane with butene-1 using liquid HF as the catalyst promoted in some instances with trifluoromethanesulfonic acid. The theoretical percent yield of product is 204. The results of these runs are shown in Table II below. The actual feed was 95 weight percent isobutane and 5 weight percent butene-1.

TABLE II
PROMOTION OF ISOBUTANE/BUTENE-1 ALKYLATION
WITH TRIFLUOROMETHANESULFONIC ACID

| Example No. | 7 | 8 | 9 | 10 | 11 | 12 | 13 | 14 | 15 |
|---|---|---|---|---|---|---|---|---|---|
| Wt. % CF$_3$SO$_3$H | 0 | 0 | 0 | 3.6 | 3.6 | 3.6 | 7.0 | 7.0 | 7.0 |
| LHSV | 20 | 40 | 80 | 20 | 40 | 80 | 20 | 40 | 80 |
| Temp. ° C. | 2 | 1.5 | 2.5 | 2.5 | 4 | 4 | 3 | 2.5 | 3 |
| % Yield | 188 | 174 | 158 | 198 | 184 | 174 | 203 | 208 | 203 |
| Estimated RON | 83.8 | 82.3 | 81.9 | 90.8 | 89.8 | 89.6 | 94.5 | 93.8 | 90.4 |
| Alkylate Composition (Wt %) | | | | | | | | | |
| Isopentane | 0.9 | 0.8 | 0.9 | 1.6 | 1.9 | 2.0 | 1.6 | 1.8 | 2.4 |
| Hexanes | 1.2 | 1.3 | 1.9 | 1.5 | 1.7 | 2.0 | 2.2 | 1.4 | 1.7 |
| Heptanes | 0.9 | 0.9 | 0.9 | 1.2 | 1.4 | 1.4 | 1.2 | 1.5 | 2.0 |
| Trimethylpentanes | 40.2 | 34.5 | 32.4 | 62.3 | 59.0 | 56.7 | 75.0 | 72.0 | 59.9 |
| Dimethylhexanes | 48.9 | 48.7 | 47.8 | 31.1 | 33.0 | 30.4 | 18.2 | 19.7 | 25.0 |
| Heavies | 7.8 | 13.7 | 16.5 | 1.9 | 2.9 | 7.3 | 2.9 | 3.6 | 9.0 |

Referring to Table II, it is again seen that increased amounts of trimethylpentanes and increased yields are both achieved using the promoter of this invention. The estimated research octane number shows an increase due to the formation of more of the desired higher octane number isomers. It should also be noted that less of the undesired heavy material was made when the promoters of this invention were employed.

A third series of runs was made to illustrate the use of isobutane with a mixed olefin stream. The feed consisted of 90 weight percent isobutane; 4.2 weight percent propylene; 3.5 weight percent isobutylene; 1.8 weight percent butene-2; and 0.5 weight percent butene-1. The theoretical percent yield is 218. The results of this series of runs again at a temperature of about 5° C. are summarized in Table III below.

TABLE III
PROMOTION OF HF ALKYLATION ISOBUTANE - MIXED OLEFINS

| Ex. No. | 16 | 17 | 18 | 19 | 20 | 21 |
|---|---|---|---|---|---|---|
| Wt % $CF_3SO_3H$ | 0 | 0 | 0 | 7.4 | 7.4 | 7.4 |
| LHSV | 20 | 40 | 80 | 20 | 40 | 80 |
| Temp. °C. | 2.5 | 4 | 5 | 2.5 | 4 | 5 |
| % Yield | 220 | 202 | 170 | 220 | 228 | 212 |
| Estimated RON | 92.0 | 91.0 | 90.2 | 94.1 | 93.2 | 91.4 |
| Alkylate Composition (wt %) | | | | | | |
| Isopentane | 4.1 | 5.2 | 5.8 | 4.5 | 4.8 | 6.4 |
| Hexanes | 4.0 | 5.0 | 5.3 | 3.8 | 4.0 | 4.8 |
| 2,4-dimethyl-pentane | 3.2 | 3.3 | 3.2 | 6.6 | 5.9 | 5.8 |
| 2,3-dimethyl-pentane | 27.9 | 26.1 | 27.4 | 20.7 | 20.7 | 19.0 |
| Trimethyl-pentanes | 42.3 | 38.1 | 33.7 | 53.0 | 49.3 | 42.4 |
| Dimethyl-hexanes | 6.1 | 7.4 | 6.7 | 5.3 | 5.2 | 5.3 |
| Heavies | 12.3 | 14.7 | 17.8 | 6.7 | 9.9 | 16.2 |

Referring to Table III, it is observed that increased quantities of trimethylpentanes are obtained and increased octane number products and higher yields are achieved at increased space velocities showing the increased activity characteristics of the HF—$CF_3SO_3H$ mixture of this invention.

Several series of runs were then made using as the charge stock a mixture of isobutane and a $C_3$–$C_5$ refinery stream from a commercial catalytic cracking unit. The composition of the $C_3$–$C_5$ refinery stream is given in Table IV below.

TABLE IV
$C_3$–$C_5$ REFINERY STREAM

| Component | Vol % |
|---|---|
| Ethane | 0.06 |
| Propane | 13.26 |
| Propene | 27.34 |
| Isobutane | 19.55 |
| N-butane | 4.71 |
| Butene-1 | 4.44 |
| Isobutene | 4.64 |
| Trans-butene-2 | 5.20 |
| Cis-butene-2 | 3.40 |
| Iospentane | 12.28 |
| N-pentane | 0.61 |
| Pentene-1 | 0.60 |
| Cis and trans pentene-2 | 1.26 |
| 2-methylbutene-1 | 1.35 |
| 2-methylbutene-2 | 0.90 |

Sufficient isobutane was blended with the $C_3$–$C_5$ refinery stream so that the molar ratio of isobutane to total olefins in the blend was 12:1.

The first series of runs was made at 4° C. using varying concentrations of promoter. The results are shown in Table V below.

TABLE V
ALKYLATION OF ISOBUTANE WITH $C_3$–$C_5$ REFINERY STREAM AT 4° C.

| Ex. No. | 22 | 23 | 24 | 25 |
|---|---|---|---|---|
| Wt % $CF_3SO_3H$ | 0 | 2.7 | 67.5 | 8.6 |
| LHSV | 40 | 40 | 40 | 40 |
| Temp. °C. | 4 | 4 | 4 | 4 |
| % Yield | 181.5 | 204.5 | 211.1 | 216.9 |
| Estimated RON | 91.3 | 92.4 | 93.1 | 92.9 |
| Exp. RON | 92.1 | 92.9 | 93.9 | 93.7 |
| Alkylate Composition (wt %) | | | | |
| Pentanes | 19.1 | 18.8 | 18.9 | 17.1 |
| Hexanes | 2.7 | 2.4 | 2.3 | 2.0 |
| 2,4-dimethyl-pentane | 2.3 | 2.9 | 3.1 | 4.4 |
| 2,3-dimethyl-pentane | 28.5 | 23.7 | 21.5 | 16.8 |
| Other Heptanes | 0.1 | 0.1 | 0.2 | 0.2 |
| Trimethyl-pentanes | 24.3 | 32.5 | 36.8 | 38.7 |
| Dimethylhexanes | 7.3 | 5.5 | 4.5 | 4.4 |
| Heavies[a] | 16.0 | 14.0 | 12.7 | 16.3 |

[a]$C_9$ and higher

Referring to Table V it can be seen that the percent yield of alkylate increases as the weight percent $CF_3SO_3H$ increases. The theoretical percent yield is 221. The RON of the product appears to optimize at a promoter level of about 7%. In this Table V and in Tables VI and VII below, the "% Yield" of alkylate was calculated by dividing the weight of the alkylate fraction minus the weight of $C_5$ paraffins in the original $C_3$–$C_5$ refinery stream by the weight of olefins in the original feed. The weight of $C_5$ paraffins in the original feed was subtracted on the realistic assumption that very little of the isopentane and pentane in the feed reacted with the olefins in the feed. This assumption is realistic, as noted earlier, due to the more reactive nature of isobutane and the great excess of isobutane which is present in the reaction zone. "Exp. RON" in this and other Tables means experimentally obtained RON on a test engine in accordance with ASTM Test D2699.

A second series of runs was made using the isobutane - $C_3$–$C_5$ refinery stream at temperatures of 14° C. and 27° C. The results are summarized in Table VI below.

TABLE VI
ALKYLATION OF ISOBUTANE WITH $C_3$–$C_5$ REFINERY STREAM AT 14° C. & 27° C.

| Ex. No. | 26 | 27 | 28 | 29 |
|---|---|---|---|---|
| Wt. % $CF_3SO_3H$ | 0 | 6.5 | 0 | 6.5 |
| LHSV | 40 | 40 | 40 | 40 |
| Temp. °C. | 14 | 14 | 27 | 27 |
| % Yield | 202.6 | 214.9 | 206.4 | 220.8 |
| Exp. Ron | 92.6 | 93.6 | 92.0 | 92.5 |
| Alkylate Composition (wt %) | | | | |
| Pentanes | 18.9 | 21.0 | 18.8 | 19.7 |
| Hexanes | 2.4 | 2.2 | 2.7 | 3.1 |
| 2,4-dimethyl-pentane | 3.2 | 4.7 | 5.7 | 7.5 |
| 2,3-dimethyl-pentane | 23.1 | 13.0 | 19.4 | 10.6 |
| Other heptanes | 0.1 | 0.5 | 0.7 | 0.7 |
| Trimethyl-pentanels | 30.8 | 41.2 | 32.1 | 38.0 |
| Dimethylhexanes | 7.1 | 5.6 | 7.3 | 6.9 |
| Heavies[a] | 14.6 | 11.7 | 13.2 | 13.3 |

[a]$C_9$ and higher

Referring to Table VI, increased percent yields and RON's are both obtained at both temperatures using 6.5% $CF_3SO_3H$.

EXAMPLE 30

The run for this Example was similar to the run for Example 22 above except the liquid hourly space velocity was 80; the temperature was from −1° C. to 3° C.; and the catalyst was liquid $CF_3SO_3H$ in lieu of liquid HF. Again, the volume ratio of liquid $CF_3SO_3H$ to total hydrocarbon in the reactor was about 1:1. The results of this run are shown in Table VII below:

TABLEW VII

| Sample | 1 | 2 | 3 |
|---|---|---|---|
| Time (min.) | 15-22½ | 45-52½ | 75-82½ |
| Temperature °C. | 3 | −1 | −1 |
| LHSV | 80 | 80 | 80 |
| Estimated RON | 91.5 | 88.3 | — |
| % Yield | 202 | 161 | trace |
| Alkylate Composition (wt %) | | | |
| Pentanes | 20.9 | 27.3 | |
| Hexanes | 4.7 | 6.3 | |
| 2,4-dimethylpentanes | 6.0 | 3.6 | |
| 2,3-dimethylpentanes | 5.7 | 3.6 | |
| Other Heptanes | 1.0 | 1.2 | |
| Trimethylpentaneks | 35.1 | 8.9 | |
| Dimethylpentanes | 5.2 | 3.3 | |
| Heavies | 19.9 | 44.6 | |

Referring to Table VII above, it can be seen that the reaction was very short-lived.

With regard to Example 30 above, the product stream was sampled as indicated during the run. With each successive sample, alkylate yield quality decreased. After only 75 minutes on-stream, very little alkylate was being produced, and it was observed that the $CF_3SO_3H$ phase has been converted almost entirely to a thick red oil.

In the runs for the experiments in Table V, 120 volumes of feed were processed without any indication of a decrease in the activity of the catalyst system, whereas in Example 30 above, the catalyst ($CF_3SO_3H$) was essentially dead after processing about 100 volumes of the same feed at about the same temperature. In addition, the yield and quality (estimated RON) of the alkylate produced using $CF_3SO_3H$ as the catalyst (Example 30) was inferior to that obtained with the $CF_3SO_3H$ promoted HF system of this invention (Examples 22-25). The inferior quality alkylate using $CF_3SO_3H$ alone is due in part to the presence of increased amounts of "heavies", "pentanes", and "hexanes" and 2,4-dimethylpentane, all of which have relatively low octane numbers.

In all of the runs reported above utilizing HF alone or in combination with $CF_3SO_3H$, the catalyst remained active throughout the 3 hour runs.

Studies were also made to show the effect of $CF_3SO_3H$ on the sulfuric acid catalyzed alkylation of isobutane with the mixture of olefins shown in Table IV above utilizing the same procedure as in Example 30. A larger volume autoclave was employed because a longer contact time was required to complete the reaction. The sulfuric acid used in the experiments reported below was in the form of concentrated sulfuric acid (96% $H_2SO_4$). The results are studied on Table VIII below.

TABLE VIII

Effect of $CF_3SO_3H$ on the $H_2SO_4$ Catalyzed Alkylation of Isobutane with a $C_3$-$C_5$ Refinery Stream

| Example No. | 31 | 32 |
|---|---|---|
| Wt % $CF_3SO_3H$ added | 0 | 6.5 |
| Temperature °C. | 30 | 30 |
| LHSV | 1.2 | 1.2 |
| % Yield | 198 | 205 |
| Estimated RON | 90.1 | 90.2 |
| Alkylate Composition (wt %) | | |
| Pentanes | 21.9 | 21.9 |
| Hexanes | 6.2 | 6.5 |
| 2,4-dimethylpentane | 10.7 | 11.6 |
| 2,3-dimethylpentane | 13.4 | 13.8 |
| Other Heptanes | 1.6 | 1.7 |
| Trimethylpentanes | 23.3 | 24.4 |
| Dimethylhexanes | 6.4 | 6.5 |
| Heavies | 16.0 | 13.2 |

Referring to Table VIII, it can be seen that the addition of $CF_3SO_3H$ has very little effect on the sulfuric acid catalyzed alkylation reaction.

EXPERIMENTAL WORK RELATING TO PROMOTION WITH $FSO_3H$

The procedure for the runs illustrating the use of $FSO_3H$ as a promoter was the same as that described above for the runs for Examples 22-25.

In a first series of runs, the $C_3$-$C_5$ refinery stream whose composition is as shown in Table IV above was blended with CP grade isobutane. The composition of the resulting blend is as shown in Table IX below.

TABLE IX

Anlaysis of Alkylation Feed

| | Wt % |
|---|---|
| Propane | 2.15 |
| Propylene | 4.17 |
| Isobutane | 86.71 |
| Normal Butane | 1.00 |
| Butene-1 | 0.70 |
| Trans-Butene-2 | 0.76 |
| Cis-Butene-2 | 0.61 |
| Isobutylene | 0.99 |
| Isopentane | 2.06 |
| Normal Pentane | 0.10 |
| $C_5$ Olefins | 0.75 |

The olefin-isobutane blend shown in Table IX above was alkylated in a series of runs using HF as the sole catalyst at varying temperatures. The results of this series of runs are given in Table X below.

TABLE X

HF ALKYLATION OF THE FEED SHOWN IN TABLE IX ABOVE WITHOUT PROMOTER

| Example No. | 33 | 34 | 35 | 36 | 37 | 38 | 39 | 40 | 41 |
|---|---|---|---|---|---|---|---|---|---|
| Temperature °C | 4 | 10 | 12 | 15 | 20 | 27 | 32 | 38 | 45 |
| LHSV | 60 | 60 | 60 | 60 | 60 | 60 | 60 | 60 | 60 |
| Yield, Wt % | 172 | 179 | 185 | 198 | 193 | 206 | 207 | 208 | 204 |
| Exp. RON | 92.3 | 92.4 | 92.4 | 92.6 | 92.6 | 92.5 | 92.4 | 92.1 | 91.8 |
| Alkylate Composition (wt %) | | | | | | | | | |
| Pentanes | 19.1 | 19.2 | 19.0 | 18.2 | 17.7 | 18.8 | 18.8 | 18.9 | 19.0 |
| Hexanes | 2.8 | 3.1 | 2.9 | 2.6 | 2.6 | 2.8 | 2.9 | 3.1 | 3.7 |
| 2,4-dimethylpentane | 2.3 | 2.5 | 2.7 | 3.0 | 3.8 | 5.1 | 6.4 | 8.1 | 9.8 |
| 2,3-dimethylpentane | 30.5 | 28.4 | 27.7 | 25.9 | 24.9 | 18.9 | 18.0 | 17.5 | 16.6 |
| Other Heptanes | 0.1 | 0.2 | 0.2 | 0.2 | 0.2 | 0.4 | 0.5 | 0.8 | 1.0 |
| Trimethylpentanes | 24.5 | 25.7 | 26.9 | 31.2 | 31.5 | 33.5 | 33.1 | 32.4 | 29.8 |
| Dimethylhexanes | 7.3 | 7.4 | 7.3 | 6.7 | 7.2 | 7.3 | 6.9 | 6.4 | 7.0 |

TABLE X-continued

HF ALKYLATION OF THE FEED SHOWN IN TABLE IX ABOVE WITHOUT PROMOTER

| Example No. | 33 | 34 | 35 | 36 | 37 | 38 | 39 | 40 | 41 |
|---|---|---|---|---|---|---|---|---|---|
| Other Octanes | 0.1 | 0.1 | 0.1 | 0.1 | 0.2 | 0.2 | 0.2 | 0.2 | 0.3 |
| Heavies[a] | 13.3 | 12.9 | 13.9 | 12.0 | 12.0 | 13.1 | 13.3 | 13.2 | 12.9 |

[a]$C_9$ and higher

A series of runs was then made to show the effect of added $FSO_3H$ on the HF catalyzed alkylation of the same feedstock and utilizing the same procedure as the runs summarized in Table X above. All of the runs in this series were made at 4° C. The purpose of these runs was to determine the optimum amount of $FSO_3H$ to employ under these conditions. The results of these runs are shown in Table XI below.

TABLE XI

EFFECT OF ADDED $FSO_3H$ ON THE ALKYLATION OF THE TABLE IX FEED AT 4° C.

| Example No. | 33 | 42 | 43 | 44 | 45 | 46 | 47 | 48 | 57 |
|---|---|---|---|---|---|---|---|---|---|
| Catalyst Composition (wt %) | | | | | | | | | |
| $FSO_3H$ | — | 3.3 | 6.6 | 9.7 | 15.7 | 21.8 | 32.4 | 50.0 | 100 |
| HF | 100.0 | 96.7 | 93.4 | 90.3 | 84.3 | 78.2 | 67.6 | 50.0 | — |
| LHSV | 60 | 60 | 60 | 60 | 60 | 60 | 60 | 60 | 60 |
| Yield, Wt % | 172 | 191 | 206 | 208 | 215 | 210 | 213 | 204 | 204 |
| Exp. RON | 92.3 | 93.0 | 93.6 | 93.9 | 93.6 | 93.2 | 92.6 | 91.9 | 90.1 |
| Alkylate Composition (wt %) | | | | | | | | | |
| Pentanes | 19.1 | 18.8 | 19.6 | 18.0 | 18.7 | 19.6 | 19.9 | 21.1 | 26.5 |
| Hexanes | 2.8 | 2.7 | 2.7 | 2.4 | 2.5 | 3.3 | 3.7 | 4.1 | 6.0 |
| 2,4-dimethyl-pentane | 2.3 | 3.3 | 4.1 | 4.2 | 5.8 | 5.8 | 6.3 | 6.9 | 5.2 |
| 2,3-dimethyl-pentane | 30.5 | 24.9 | 21.2 | 21.3 | 10.5 | 8.6 | 8.2 | 7.4 | 5.8 |
| Other Heptanes | 0.1 | 0.1 | 0.1 | 0.3 | 0.7 | 0.6 | 0.9 | 1.3 | 1.9 |
| Trimethyl-pentanes | 24.5 | 31.8 | 36.1 | 36.7 | 41.0 | 38.4 | 36.8 | 32.9 | 23.1 |
| Dimethylhexanes | 7.3 | 6.0 | 4.6 | 4.0 | 5.1 | 5.7 | 6.4 | 6.5 | 8.1 |
| Other Octanes | 0.1 | 0.1 | 0.0 | 0.0 | 0.1 | 0.2 | 0.2 | 0.2 | 0.9 |
| Heavies[a] | 13.3 | 12.4 | 11.3 | 12.9 | 15.4 | 17.7 | 17.4 | 19.6 | 22.5 |

[a]$C_9$ and higher

Referring to Table XI above, it can be observed that the best quality alkylate was made in Example 44 utilizing 9.7 weight percent $FSO_3H$.

A further series of runs was made at varying temperatures utilizing the same feed stock and procedures used for the Examples summarized in Tables X and XI above, employing as the catalyst system a mixture of 9.7 weight percent $FSO_3H$ in liquid HF. The results of this further series of runs are summarized on Table XII below.

TABLE XII

HF ALKYLATION OF TABLE IX FEED PROMOTED BY 9.7 WT % $FSO_3H$

| Example No. | 44 | 49 | 50 | 51 | 52 | 53 | 54 | 55 | 56 |
|---|---|---|---|---|---|---|---|---|---|
| Temperature ° C. | 4 | 7 | 10 | 16 | 20 | 25 | 32 | 38 | 45 |
| LHSV | 60 | 60 | 60 | 60 | 60 | 60 | 60 | 60 | 60 |
| Yield, Wt % | 208 | 205 | 222 | 210 | 210 | 213 | 212 | 207 | 203 |
| Exp. RON | 93.9 | 93.7 | 93.5 | 93.2 | 92.8 | 92.5 | 92.1 | 91.7 | 91.3 |
| Alkylate Composition (wt %) | | | | | | | | | |
| Pentanes | 18.0 | 17.4 | 17.7 | 17.9 | 18.2 | 18.7 | 19.1 | 19.4 | 20.0 |
| Hexanes | 2.4 | 2.6 | 2.8 | 3.2 | 3.8 | 3.9 | 4.1 | 4.1 | 4.2 |
| 2,4-dimethyl-pentane | 4.2 | 6.2 | 6.4 | 7.3 | 7.7 | 7.5 | 7.9 | 8.3 | 8.7 |
| 2,3-dimethyl-pentane | 21.3 | 15.4 | 15.3 | 13.1 | 12.0 | 10.9 | 10.1 | 9.1 | 8.5 |
| Other Heptanes | 0.3 | 0.6 | 0.7 | 0.8 | 1.1 | 1.0 | 1.2 | 1.3 | 1.5 |
| Trimethyl-pentanes | 36.7 | 39.9 | 39.1 | 38.8 | 37.0 | 36.9 | 34.1 | 32.7 | 30.0 |
| Dimethylhexanes | 4.0 | 5.0 | 5.3 | 5.7 | 6.2 | 6.8 | 7.4 | 8.3 | 9.2 |
| Other Octanes | 0.0 | 0.1 | 0.2 | 0.1 | 0.2 | 0.2 | 0.3 | 0.3 | 0.4 |
| Heavies[a] | 12.9 | 12.5 | 12.5 | 12.9 | 13.5 | 14.1 | 15.8 | 16.5 | 17.5 |

[a]$C_9$ and higher

A comparison of the results in Tables X and XII shows the improvement in both yield and/or quality of alkylate (RON) at temperatures below about 30° C. At the preferred lower temperature of 20° C. and less, both the yield and the quality of the alkylate are improved.

EXAMPLE 57

Example 48 was repeated except no HF was employed. The catalyst system was 100 percent $FSO_3H$. The volume ratio of catalyst to hydrocarbon in the reactor was 1:1, as in all the other runs. The yield of alkylate was 204 weight percent based on the olefin in the feed. The experimental research octane number was 90.1. The results are summarized in Table XI above.

A comparison of the results of the runs in Table XI shows the unexpected improvement of the HF—FSO$_3$H catalyst system. Using HF along (Example 33) the RON of the alkylate product was 92.3. Using FSO$_3$H alone, the RON of the alkylate product was 90.1 (Example 57). The yield of alkylate using FSO$_3$H was higher (204 weight percent versus 172) showing a faster rate of reaction using the FSO$_2$H. It might be expected that a combination of HF and FSO$_3$H would result in an increased rate of reaction (increased yield) over HF alone with a corresponding decrease in alkylate quality over HF alone. Surprisingly, the addition of FSO$_3$H resulted in not only an increase in quality of alkylate as measured by RON but also the yield increased when the FSO$_3$H concentration in the feed was from 6 to 30 weight percent, especially 15 to about 30 percent of the total catalyst system.

Resort may be had to such variations and modifications as fall within the spirit of the invention and the scope of the appended claims.

I claim:

1. A process for the alkylation of an isoparaffin having from 4 to 5 carbon atoms per molecule with an olefinic hydrocarbon charge stock comprising at least one monoolefin selected from the group consisting of propylene, butene-1, pentene-1 and hexene-1, which comprises:

reacting at least one of said isoparaffins with at least one of said monoolefins in the presence of a catalyst system comprising hydrogen fluoride and from 0.1 to 30 weight percent of trifluoromethanesulfonic acid based on the total weight of the catalyst system;

under reaction conditions including a temperature from −20° C. to 30° C. and a reaction pressure sufficient to maintain the hydrogen fluoride in the liquid phase.

2. A process is accordance with claim 1 wherein the molar ratio of the isoparaffin to monoolefin entering the reaction zone is from 5:1 to 100:1, and the volume of the hydrocarbon charge to the acid catalyst is from 0.1:1 to 10:1.

3. A process in accordance with claim 2 wherein the reaction temperature is from 0° to 20° C. and the amount of said trifluoromethanesulfonic acid is from 4 to 20 weight percent.

4. In a process for the alkylation of isobutane with an olefinic hydrocarbon charge stock comprising at least one monoolefin selected from the group consisting of propylene, butene-1, pentene-1 and hexene-1 and wherein said alkylation is conducted in the presence of a catalyst comprising HF under reaction conditions including a reaction temperature from −20° C. to 30° C. and a pressure sufficient to maintain the HF in the liquid phase, the improvement which comprises conducting said alkylation process in the added presence of from 0.1 to 30 weight percent of trifluoromethanesulfonic acid based on the total weight of said catalyst and said trifluoromethanesulfonic acid.

5. A process according to claim 4 wherein the amount of said trifluoromethanesulfonic acid is from 2 to 30 weight percent of the total weight of said catalyst and said trifluoromethanesulfonic acid the reaction temperature is from 0° to 20° C. and the molar ratio of the isobutane to monoolefin entering the reaction zone is from 5:1 to 100:1.

6. A process according to claim 5 wherein the olefinic hydrocarbon is propylene.

7. A process in accordance with claim 5 wherein the olefinic hydrocarbon charge is a mixture of olefins having from 3 to 4 carbon atoms.

8. A process according to claim 5 wherein the olefinic hydrocarbon charge stock comprises a refinery C$_3$-C$_5$ stream derived from the catalytic cracking of petroleum hydrocarbons.

* * * * *

UNITED STATES PATENT OFFICE
CERTIFICATE OF CORRECTION

Patent No. 4,118,433  Dated  October 3, 1978

Inventor(s) Robert A. Innes

It is certified that error appears in the above-identified patent and that said Letters Patent are hereby corrected as shown below:

Col. 1, line 38, "expanded" should be --expended--;

Col. 1, line 63, "by" should be --be--;

Col. 3, line 13, "line 4" should be --line 14--;

Col. 6, line 19, "member" should be --number--;

Col. 13, line 3, "along" should be --alone--;

Col. 13, line 8, "$FSO_2H$" should be --$FSO_3H$--.

Signed and Sealed this

Nineteenth Day of June 1979

[SEAL]

Attest:

RUTH C. MASON
Attesting Officer

DONALD W. BANNER
Commissioner of Patents and Trademarks